United States Patent
Banks et al.

(10) Patent No.: US 6,737,525 B2
(45) Date of Patent: *May 18, 2004

(54) ELECTROPHILIC FLUORINATION

(75) Inventors: Ronald Eric Banks, Stockport (GB); Mohamed Khalifa Besheesh, High Peak (GB)

(73) Assignee: Air Products and Chemicals, Inc., Allentown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/044,049

(22) Filed: Oct. 23, 2001

(65) Prior Publication Data

US 2002/0123657 A1 Sep. 5, 2002

(30) Foreign Application Priority Data

Oct. 24, 2000 (GB) .............................. 0026012

(51) Int. Cl.$^7$ ........................................... C07D 253/00
(52) U.S. Cl. ........................ 544/182; 544/66; 544/180
(58) Field of Search ........................... 544/66, 180, 182

(56) References Cited

U.S. PATENT DOCUMENTS

| | | | |
|---|---|---|---|
| 4,828,764 A | 5/1989 | DesMarteau | 260/397 |
| 4,996,320 A | 2/1991 | Umemoto et al. | |
| 5,081,249 A | 1/1992 | Umemoto | |
| 5,086,178 A | 2/1992 | Banks | |
| 5,336,772 A | 8/1994 | Saiki et al. | |
| 5,367,071 A | 11/1994 | Syvret | |
| 5,459,267 A | 10/1995 | Poss et al. | |
| 5,473,065 A | 12/1995 | Banks | |
| 5,631,372 A | 5/1997 | Poss et al. | |
| 6,069,114 A | 5/2000 | Lorenz et al. | |

FOREIGN PATENT DOCUMENTS

| | | |
|---|---|---|
| EP | 0204535 | 12/1986 |
| FR | 1201782 | 1/1960 |

OTHER PUBLICATIONS

Schulz et al. (DN 122:31666, CAPLUS, abstract of J. Organometallic Chemistry (1994), 480(1–2), 195–197).*
J. H. Forsberg, et al., "Lanthanide(III) Ion Catalyzed Reaction of Ammonia and Nitriles: Synthesis of 2,4,6–Trisubstituted–s–triazines," Department of Chemistry, St. Louis University, Oct. 21, 1987.
R. D. Chambers, et al., "Polyfluoroheteroaromatic Compounds," Academic Press, Inc., Advances in Heterocyclic Chemistry, Vol 28, pp 1–71.
Lal et al. "Electrophilic NF Fluorinating Agents," Chem. Rev. 1996, 96, pp1737–1755.
Furin, G. G.: Methods of Organic Chemistry (Houen–Wey): vol. E10a; Organofluorine Compounds (ed. B. Baasner, et al.), Georg Thieme Verlag, Stuttgart, 1999, pp. 432–499.

Banks, R. E.: Selectfluor™ reagent F–Teda–BF$_4$ in action: tamed fluorine at your service. Journal of Fluorine Chemistry 87 (1998) 1–17.
Broschag, Matthias, et al.: "Synthesis and characterization of novel halogeno(+I) adduct complexes containing malonitrile and 1,3,5–triazine." Inorganica Chimica Acta, (1993), 205(2), 167–73, XP001052954.
Schleyer, Paul V. R. et al.: "Preparation of 1–Fluoro–2,4, 6–trihalogeno–s–triazinium Hexafluoroarsenates: Structure of 'C$_3$N$_3$Cl$_3$F!'AsF$_6$! As Deduced by Experimental and ab Initio Methods." Inorg. Chem. (1993), 32(8), 1523–4, XP001041857.
Schulz, A., et al.: Das Perfluortiazinium–Kaion als Oxidationsmittel in der metallorganischen Synthese—Ein neuer Weg zur Darstellung von (Cp$_2$MCl$_2$)$^{2+}$(M=Mo,W). Journal of Organometallic Chemistry, 480 (1994) 195–197.
Broschag, M. et al.: "Fluorination of cyanuric chloride and low–temperature crystal structure of '(ClCN)$_3$F!+'AsF$_6$!–." Z. Anorg. Allg. Chem. (1994), 620(6), 1132–6, XP001052965.
Banks, R. E., et al.: N–Halogeno compounds. Part 18. 1–Alkyl–4–fluoro–1,4–diazoniabicyclo[2.2.2]octane salts: user–friendly site–selective electrophilic fluorinating agents of the N–fluoroammonium class. J. Chem. Soc. Perkin Trans. 1, 1996, 2069.

* cited by examiner

*Primary Examiner*—Sabiha Qazi
(74) *Attorney, Agent, or Firm*—Michael Leach

(57) ABSTRACT

N-fluorotriazinium salts, especially those of the following Formula I, are electrophilic fluorinating agents useful in fluorinating, preferably in a nitromethane solvent, carbanionic species and/or activated aromatic compounds:

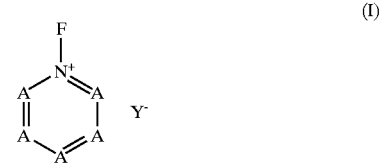

(I)

wherein three A moieties are independently CR, where each R is, independently, hydrogen, halogen, (primary, secondary or tertiary) amino, hydroxyl, amino, cyano, perfluorothio hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups; two A moieties are independently Z, where each Z is independently nitrogen or a quaternary nitrogen atom and Y is a counterion or group of counterions which are inert to chemical attack by fluorine, and oligomers or polymers thereof in which adjacent triazinium moieties are linked by a common R substituent. Preferably the cation of the salt is 2,4,6-trichloro-1,3,5-triazinium.

24 Claims, No Drawings

ELECTROPHILIC FLUORINATION

CROSS REFERENCES TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates to electrophilic fluorination and in particular to the use of N-fluorotriazinium salts as electrophilic fluorinating agents. The invention provides a method of electophilically fluorinating a substrate, especially an organic substrate using N-fluorotriazinium salt fluorinating agents and has particularly, but not exclusive, application to the fluorination of electron-rich species, for example activated aromatic compounds (i.e. carrying electron-donating substituents) or overt or covert carbanions. At least the preferred tri(halo or trifluoromethyl)-substituted N-fluorotriazinium salts are sufficiently strong fluorinating agents to readily fluorinate unsubstituted aromatic substrates and aromatic substrates having one or more electron-withdrawing substituents.

Fluorination is an important process in many areas of industry, in particular where the synthesis of specialty chemicals is concerned. Known fluorination methods are conveniently categorized according to the perceived manner in which the fluorinating agents provide fluorine for combination with an active site in an organic molecule, namely as fluorine atom (F·), fluoride ion (F−) or, conceptually, fluoronium ion (F+). Fluorinations involving fluorine atom are notoriously exothermic and non-selective, hence "light" strategic fluorination of organic compounds (that is, the introduction of one or two fluorine substituents or a trifluoromethyl group at key molecular sites) rests on the availability of versatile ranges of nucleophilic and electrophilic sources of fluorine. Of late, the use of N-fluoro compounds has become one of the most widely used methods for the selective formation of carbon-fluorine bonds via "electrophilic" mechanisms. A recent comprehensive review of this synthetic methodology contains no reference to N—F reagents derived from triazines (see G. G. Furin in Methods of Organic Chemistry (Houben-Weyl): Volume E10a; Organofluorine Compounds (ed. B. Baasner, H. Hagemann, and J. C. Tatlow), Georg Thieme Verlag, Stuttgart, 1999, pp. 432–499.

1-Chloromethyl-4-fluoro-1,4-diazoniabicyclo[2.2.2] octane bis(tetrafluoroborate) (so-called F-TEDA-BF$_4$) is a known, commercially available (under the trade name "Selectfluor") fluorinating agent and is useful as a general purpose fluorinating agent. However this material has only a moderate fluorinating power and is able to fluorinate benzene only under forcing conditions, for example under reflux for 24 hours. The chemistry of F-TEDA-BF$_4$ has been reviewed by R. E. Banks in J. Fluorine Chemistry 87 (1998) 1–17, the whole content of which is incorporated herein by reference.

N-Fluoropyridinium salts and ring-substituted analogues thereof, e.g. N-fluoropyridinium triflate, are known for use as a fluorinating agent but have relatively low fluorinating power. U.S. Pat. No. 4,828,764 discloses that certain N-fluoro-N-perfluoroalkyl or perfluoroaryl sulfonamides formula $R_fSO_2NFR$ are electrophilic fluorinating agents. In this formula $R_f$ represents a perfluorinated $C_1$–$C_{30}$ alkyl, $C_3$–$C_{30}$ cycloalkyl, $C_6$–$C_{14}$ aryl substituted $C_1$–$C_{10}$ alkyl or a $C_6$–$C_{14}$ aryl group and R represents a $C_1$–$C_{30}$ alkyl, $C_3$–$C_{30}$ cycloalkyl, $C_6$–C14 aryl substituted $C_1$–$C_{10}$ alkyl, or $C_6$–$C_{14}$ aryl group optionally substituted with one or more inert substituents including, inter alia, fluorine and, when $R_f$ is trifluoromethyl, R alternatively can represent perfluoromethyl-sulfonamido. The preferred fluorinating agents are stated to be N-fluorobis-(trifluoromethanesulfonyl)imide ($R_f$=CF$_3$ and R=CF$_3$SO$_2$), known as DesMarteau's Reagent, and N-fluoro-N-methyltrifluoromethanesulfonamide ($R_f$=CF$_3$ and R=CH$_3$). DesMarteau's Reagent is a powerful electrophilic fluorinating agent which is capable of converting benzene to fluorobenzene at room temperature but is hazardous, time-consuming and expensive to prepare requiring eight or nine reaction steps from readily available material. Only a very limited number of other known fluorinating agents are strong enough to fluorinate benzene without forcing conditions but they often provide relatively low yields or require special precautions. Those reported to fluorinate benzene include, in addition to DesMarteau's Reagent, CF$_3$OF, XeF$_2$, NF$_4^+$BF$_4^-$, N$_2$F$^+$AsF$_6^-$, N-fluoropentachloropyridinium triflate, perfluoro-[N-fluoro-N-(4-pyridyl) methanesulfonamide] and N-fluoro-2,6-bis (methoxycarbonyl)pyridinium triflate. Very few of these compounds, only NF$_4^+$BF$_4^-$ and XeF$_2$, are known to fluorinate aromatic substrates having electron-withdrawing substituents such as nitrobenzene.

N-Fluorotriazinium salts of the following Formula A are known:

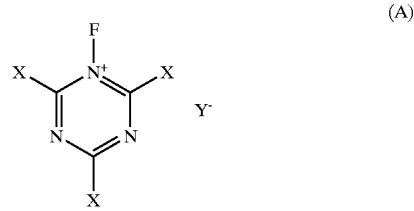

(A)

wherein:
(i) X=H&Y$^-$=AsF$_6^-$(Ref. 1—see below)
(ii) X=F&Y$^-$=AsF$_6^-$(Ref. 2—see below)
(iii) X=F&Y$^-$=BF$_4^-$(Ref. 3—see below) and
(iv) X=Cl&Y$^-$=AsF$_6^-$(Refs. 2 & 4—see below).

The N-fluorotriazinium salts of Formula A are reported to be oxidizing agents of use in, for example, organometallic chemistry. The cationic component of compounds of Formula A in which X is H, F and Cl have been described as "oxidative fluorinators" and a qualitative scale for their oxidizing strength and that of NF$_4^+$ has been computed ab initio (Ref. 3—see below).

Ref. 1=Broschag et al. Inorg. Chim. Acta, 205 (1993) 167–173;

Ref. 2=Schleyer et al. Inorg. Chem. 32 (1993) 1523–1524;

Ref. 3=Schulz and Klapötke J. Organometal. Chem. 480 (1994) 195–197; and

Ref. 4=Broschag et al. Z. Anorg. Allg. Chem., 620 (1994) 1132–1136.

There is a statement in Schleyer et al. that 1-fluoro-2,4, 6-trichloro-s-triazinium hexafluoroarsenate (Formula A; X=Cl; and Y$^-$=AsF$_6^-$) "is a promising fluorination agent"

but no further details were provided or subsequently reported. It is believed that uses of the compounds of Formula A other than as oxidizing agents was not contemplated or investigated. In particular, there is no disclosure in the prior art of any of these compounds being evaluated as oxidative fluorinators (as distinct from non-fluorinating oxidizing agents) despite the computed values reported in Refs. 3 and 4.

A copending US Patent Application of even date corresponding to and claiming priority from UK Patent No. 0026010.9 (filed Oct. 24th 2000) discloses and claims electrophilic fluorinating agents which are triazinium compounds of the following Formula B:

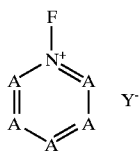

(B)

wherein:
three A moieties are independently CR, where each R is independently, hydrogen, halogen, hydroxyl, (primary, secondary or tertiary) amino, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups, and at least one R is neither hydrogen nor halogen;

two A moieties are independently Z, where each Z is independently nitrogen or a quaternary nitrogen atom; and $Y^-$ is a counterion or group of counterions which are inert to chemical attack by fluorine, and oligomers or polymers thereof in which adjacent triazinium moieties are linked by a common R substituent.

BRIEF SUMMARY OF THE INVENTION

We have now found that N-fluorinated triazinium salts are excellent electrophilic fluorinating agents yet do not possess some of the drawbacks of known electrophilic fluorinating agents. These salts have a high fluorinating power which allows substrates which are difficult to fluorinate using known fluorinating agents to be fluorinated, especially electron-rich species such as, for example, carbanionic and/or activated aromatic substrates. Also they may be employed to fluorinate substrates which may presently be fluorinated electrophilically using known fluorinating agents but under milder reaction conditions due to the effective fluorinating power of the N-fluorotriazinium cation.

The preferred N-fluorotriazinium salts can be presented by the following Formula I:

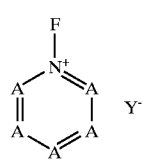

(I)

in which:
three A moieties are independently CR, where each R is independently, hydrogen, halogen, hydroxyl, (primary, secondary or tertiary) amino, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

two A moieties are independently Z, where each Z is independently nitrogen or a quaternary nitrogen atom; and $Y^-$ is a counterion or group of counterions which are inert to chemical attack by fluorine.

Other preferred salts are oligomers or polymers of the monomers of Formula I in which adjacent triazinium moieties are linked by a common R substituent.

DETAILED DESCRIPTION OF THE INVENTION

In its broadest aspect, the present invention provides a method of electrophilic fluorination which comprises contacting an organic substrate with a N-fluorotriazinium salt electrophilic fluorinating agent.

In another aspect of the invention there is provided use of a N-fluorotriazinium salt as an electrophilic fluorinating agent.

N-Fluorotriazinium salts have a high fluorinating power which allows substrates which are difficult to fluorinate using known fluorinating agents to be fluorinated especially electron-rich species for example carbanionic and/or activated aromatic substrates. Also they may be employed to fluorinate substrates which may presently be fluorinated electrophilically using known fluorinating agents but under milder reaction conditions due to the effective fluorinating power of the N-fluorotriazinium cation.

Suitably, the N-fluorotriazinium salts are of the following Formula I:

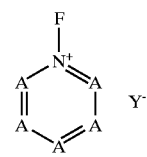

(I)

wherein:
three A moieties are independently CR, where each R is independently, hydrogen, halogen, hydroxyl, (primary, secondary or tertiary) amino, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

two A moieties are independently Z, where each Z is independently nitrogen or a quaternary nitrogen atom; and $Y^-$ is a counterion or group of counterions which are inert to chemical attack by fluorine, and oligomers or polymers thereof in which adjacent triazinium moieties are linked by a common R substituent.

It is presently preferred that the triazinium compounds are 1,2,4-triazinium compounds of the following Formula IA or, especially, 1,3,5-triazinium compounds of the following Formula IB:

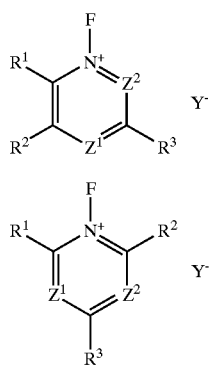

wherein:
R$^1$, R$^2$ and R$^3$ are, independently, hydrogen, halogen, (primary, secondary or tertiary) amino, hydroxyl, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

Z$^1$ and Z$^2$ are independently nitrogen or a quaternary nitrogen atom; and

Y$^-$ is a counterion or group of counterions which are inert to chemical attack by fluorine, and oligomers or polymers thereof in which adjacent triazinium moieties are linked by a common R substituent.

The presently most preferred compounds are those in which each R substituent, or each of R$^1$, R$^2$ and R$^3$ for Formulae IA and IB, is halogen or trifluoromethyl. As mentioned above, the N-fluoro-trihalotriazinium and N-fluoro-tris (trifluoromethyl)triazinium salts are remarkably strong fluorinating agents capable of room temperature fluorination of unsubstituted aromatic substrates such as benzene and aromatic substrates having one or more electron-withdrawing substituents such as chlorobenzene or nitrobenzene.

The said carbon-containing substituent(s) may be unsubstituted and contain only hydrogen and carbon atoms, and in the case of hydrocarbyloxy and hydrocarbylthio, also an oxygen or sulfur atom respectively, or they may be substituted and contain one or more heteroatoms for example oxygen, nitrogen, halogen and sulfur, and/or heterogroups, for example carbonyl, ester and amide links. Thus, optionally the carbon-containing substituent(s) may contain a heteroatom in the carbon chain and/or may be substituted with a substituent containing a heteroatom such as, for example, OH, alkoxy and halogen, for example chlorine, bromine and especially fluorine. One or more (including all) hydrogen atoms in the said carbon-containing substituent(s) may be substituted as desired.

The hydrocarbyl and hydrocarbyloxy groups may be alkyl, alkenyl, aryl, aryloxy and alkoxy groups which optionally are substituted. Preferably the alkyl and alkoxy group have from about 1 to about 12 carbon atoms, more preferably about 1 to about 8 carbon atoms and especially about 1 to about 4 carbon atoms, for example methyl, ethyl, methoxy and ethoxy. Preferably the alkenyl group and aryl group have from about 2 to about 12, especially about 2 to about 8, carbon atoms and from about 6 to about 12, especially about 6 to about 9, carbon atoms respectively.

In one embodiment, at least one R, or at least one of R$^1$, R$^2$ and R$^3$ for Formulae IA and IB, is selected from the group consisting of hydrohaloalkyl groups, especially hydrofluoroalkyl groups, and perhaloalkyl groups, especially perfluoroalkyl groups. Examples of suitable perfluoroalkyl groups include trifluoromethyl, pentafluoroethyl and perfluorooctyl groups and examples of suitable hydrofluoroalkyl groups include 2,2,2-trifluoroethyl, 2,2,3,3-tetrafluoropropyl and H(CF$_2$CF$_2$)$_p$CH$_2$ groups (where p is at least 2). Perhaloalkyl groups may be preferred in some cases due to the absence of a carbon-hydrogen bond which may be susceptible to electrophilic fluorination.

In another embodiment, preferred for ease of synthesis, at least one R, or at least one of R$^1$, R$^2$ and R$^3$ for Formulae IA and IB, is selected from the group consisting of hydrohaloalkoxy groups, especially hydrofluoroalkoxy groups, and perhaloalkyl groups, especially perfluoroalkyl groups. Examples of suitable perfluoroalkoxy groups include trifluoromethoxy, pentafluoroethoxy and perfluorooctoxy groups and examples of suitable hydrofluoroalkoxy groups include 2,2,2-trifluoroethoxy and 2,2,3,3-tetrafluoropropoxy. Particularly preferred are H(CF$_2$CF$_2$)$_p$CH$_2$O groups (where p is at least 2) which are readily available using known telomer alcohols of the corresponding formula H(CF$_2$CF$_2$)$_p$CH$_2$OH.

In another embodiment, at least one R, or R$^1$, R$^2$ and/or R$^3$ for Formulae IA and IB, is a thio analogue of the aforementioned hydrohaloalkoxy and perhaloalkoxy groups, for example trifluoromethylthio (CF$_3$S), or a perfluorothio group such as trifluorothio (SF$_3$) or pentafluorothio (SF$_5$).

The terms aryl and aryloxy include moieties which contain aliphatic as well as aromatic groups. Preferred aryl and aryloxy groups include phenyl, phenoxy, and groups of formula C$_6$H$_5$(CH$_2$)$_r$[OC$_2$H$_4$]$_q$O$_t$ where q is 0 to 6, r is 0 to 8 and t is 0 or 1, which may be optionally substituted, preferably with fluorine.

It is preferred that at least one of R, or at least one of R$^1$, R$^2$ and R$^3$ for Formulae IA and IB, is hydrocarbyl, hydrocarbyloxy, hydrohalocarbyl, hydrohalocarbyloxy, perhalocarbyl, or perhalocarbyloxy, and Z, or Z$^1$ and Z$^2$ for Formulae IA and IB, and Y$^-$ are as defined above.

It is especially preferred that all R substituents, or R$^1$, R$^2$ and R$^3$ for Formulae IA and IB, are identical in a given compound. Examples of especially preferred compounds are those in which all R substituents, or all of R$^1$, R$^2$ and R$^3$ are methyl, methoxy, trifluoromethoxy groups, or, most preferably, halogen or trifluoromethyl. A practical advantage of R$^1$, R$^2$ and R$^3$ being the same group is the manufacture of the compound may be simplified and isomers or a mixture of compounds is less likely to be produced.

R, or R$^1$, R$^2$ and R$^3$ for Formulae IA and IB, may be selected so as to provide technical advantages to the compound of Formula I in addition to the fluorination characteristics such as improving the solubility of the compound in non-polar solvents and solvents of low polarity. Thus greater flexibility in chemical synthesis involving electrophilic fluorination is also provided by the compounds of Formula I.

The compounds of Formula I can be oligomers or polymers in which adjacent triazinium moieties are linked by a common R substituent, for example, a hydrocarbyl, perfluorohydrocarbyl or hydrocarbyloxy group. Presently preferred linking groups are dioxyphenyl, di(oxycarbyl)phenyl, alkylenedioxy or bis(oxyaryl)alkylene groups, such as, for example, 1,5-dioxypent-2,4-diyl (i.e. —O—CH$_2$—CH—CH$_2$—CH—CH$_2$—O—), 1,3-bis(p-oxyphenyl)prop-1,3-diyl (i.e. -p-OC$_6$H$_4$—CH—CH$_2$—CH—C$_6$H$_4$O-p-), or 1,3-bis(m/p-oxymethylphenyl)prop-1,3-diyl (i.e. -m/p-OCH$_2$C$_6$H$_4$—CH—CH$_2$—CH—C$_6$H$_4$CH$_2$O-m/p-).

The compounds of Formula I contain at least one fluorinated quaternary nitrogen atom in the triazinium ring and one or both of the other triazinium nitrogen atoms may be quaternary, preferably fluorinated, nitrogen. In a preferred embodiment both Z, or both $Z^1$ and $Z^2$ for Formulae IA and IB, are nitrogen and the most preferred compounds are those of the following Formula II:

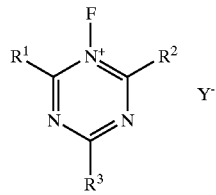

(II)

wherein $R^1$, $R^2$, $R^3$ and $Y^-$ are as defined above.

Examples of preferred compounds according to the invention are those having a triazinium cation as shown below in Formulae III to VII, especially those of Formulae IV, V and VI.

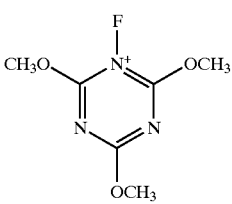

(III)

1-fluoro-2,4,6-trimethyl-1,3,5-triazinium

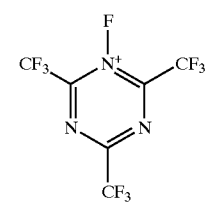

(IV)

1-fluoro-2,4,6-trimethoxy-1,3,5-triazinium

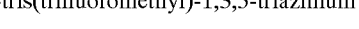

(V)

1-fluoro-2,4,6-tris(trifluoromethyl)-1,3,5-triazinium

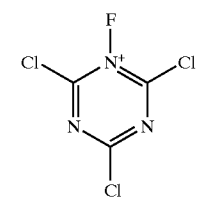

(VI)

1-fluoro-2,4,6-trichloro-1,3,5-triazinium

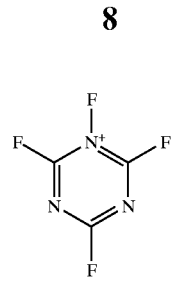

(VII)

1-fluoro-2,4,6-trifluoro-1,3,5-triazinium

The counterion $Y^-$ is resistant to chemical attack by fluorine and desirably, is thermally stable and possesses low environmental toxicity. The counterion(s) can be any anion (s) which can be counterion(s) to the triazinium cation. The counterion(s) may have a single charge or a multiple charge or be a group of counterions so as to balance the charge of the triazinium moiety. Also the counterion may be a counterion to more than one mole of the triazinium cation, for example where the cation has a single charge and the counterion has a multiple charge.

Suitably the counterion is weakly nucleophilic. Suitable anions include fluoride; fluorosulfate ($SO_3F^-$); alkanesulfonate, especially methanesulfonate ($CH_3SO_3^-$); alkyl sulfate, especially methyl sulfate ($CH_3SO_4^-$); perfluoroalkane-sulfonate, preferably triflate ($CF_3SO_3^-$) and nonaflate ($C_4F_9SO_3^-$); arenesulfonate, especially tosylate (i.e. p-toluenesulfonate; $p\text{-}CH_3C_6H_4SO_3^-$); alkanecarboxylate; perfluoroalkanecarboxylate; tetrafluoroborate ($BF_4^-$); tetraphenylborate ($Ph_4B^-$); hexafluorophosphate ($PF_6^-$); hexafluoroantimonate ($SbF_6^-$); hexafluoroarsenate ($AsF_6^-$); chlorate ($ClO_3^-$); sulfate ($SO_4^{2-}=2Y^-$); hydrogen sulfate ($HSO_4^-$) and $F(HF)_x^-$ where x is at least 1. Presently preferred counterions include fluoride, tetrafluoroborate, triflate, tosylate, hexafluoroarsenate and hexafluorophosphate.

Preferably, the compounds of Formula I are prepared using a solvent-based process which comprises contacting a triazine compound with a fluorine source under acidic conditions in a solvent which is inert under the process conditions.

Suitably the fluorine source is an electrophilic fluorine source such as, for example, fluorine gas or a mixture of fluorine gas and a neutral compound derivable from a fluorine-containing counterion $Y^-$ by removing at least one fluoride ion from $Y^-$, for example boron trifluoride. Preferably, the fluorine source is fluorine gas. While the fluorine gas may be used without dilution, in general, it is preferable to use fluorine gas diluted with an inert gas so that the volume of the inert gas is between about 99.9% and about 50% for controlling the vigorous reaction. Suitable inert gases include nitrogen, helium and argon.

The triazine compound to be fluorinated is suitably a compound of the Formula VIII and may be obtained by subjecting a compound or a mixture of compounds of formula RCN to a known process for producing a triazine compound of formula $(RCN)_3$, wherein R is independently $R^-$, $R^2$ or $R^3$ as described herein:

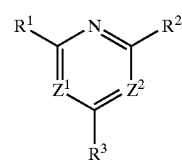

(VIII)

The fluorination process is carried out in the presence of an acid which may be a Brønsted acid (organic or mineral) or a Lewis acid. The level of acid is suitably adjusted so as to reduce and desirably avoid double protonation of the triazine compound and to provide a yield (as determined by $^{19}$F NMR) of F—N$^{30}$ of at least about 20% and desirably of at least about 50%. Desirably the molar ratio of acid to triazine substrate is about 0.5 to about 2.5, preferably about 1 to about 2.2.

Preferable examples of Brønsted acid have pKa in the range from about 12.4 to about 4.6 and include halogenated alcohols, for example chlorodifluoro-ethanol, dichlorofluoroethanol, chlorooctafluoro-t-butanol, trifluoroethanol, tetrafluoropropanol, pentafluoropropanol, hexafluoroisopropanol, octafluoro-pentathol, and nonafluoro-t-butanol. Fluorinated alcohols, particularly those which are free of chlorine, are especially preferred.

Other acids which are especially preferred include acids of the counterion Y$^-$described above, for example anhydrous hydrofluoric acid, hexafluoro-antimonic acid, tetrafluoroboric acid and triflic acid, sulfuric acid, methanesulfonic acid, acetic acid and trifluoroacetic acid.

Brønsted acids may be used in the form of a complex with ethers, water, alcohols, nitriles, carboxylic acids and the like and may be used in the form of an aqueous solution.

Preferably, the solvent is non-aqueous and it is presently particularly preferred that the solvent is acetonitrile, a halogenated, especially fluorinated, alcohol or, especially, nitromethane. In this connection, it is believed that there has not been any previous proposal to use nitromethane as a solvent, or for any other purpose, with any N—F or $^+$N—F reagent.

If desired the same material may be used as both the acid and the solvent.

The reaction to produce compound of Formula I is carried out at a temperature at which the solvent is in the liquid phase and suitably at a sufficiently low temperature that reaction due to a free radical mechanism is reduced and suitably avoided. The particular temperature selected depends on the solvent and also the reactants. By way of example only, the reaction suitably may be carried out at a temperature of about −40 to about 10° C. A temperature of about −40 to about −20° C. is preferred for acetonitrile and a temperature of about −10 to about 5° C. is preferred for hexafluoroisopropyl alcohol. The reaction may be carried out at elevated pressure although this is not essential.

Fluorination of the triazine compound may be carried out using a stirred-tank batch reactor. Where the fluorine source is gaseous, the fluorine source is suitably admitted either as neat gas at sub-atmospheric pressure or as a continuous flow of fluorine blended with nitrogen or other inert diluent at about atmospheric pressure. Advantageously, the process for producing compound of Formula I may be operated as a continuous process.

The invention also provides a method of producing a fluorinated substrate which comprises contacting a substrate with a compound of Formula I so as to fluorinate the substrate.

The compounds of Formula I may be used as electrophilic fluorinating agents in a similar manner to Selectfluo™ and in manner know in the art (see, for example, R. E. Banks et al. J. Chem. Soc. Perkin Trans. I, 1996, 2069). The fluorinating agent may be contacted with the substrate neat and optionally at elevated temperature. If desired the fluorination process may be carried out in a solvent, for example acetonitrile or, especially, nitromethane. As mentioned above, it is believed that there has not been any previous proposal to use nitromethane as a solvent, or for any other purpose, with any N—F or $^+$N—F reagent.

When a compound of Formula I has been used in a fluorination reaction and so depleted in fluorine, it may be recovered and regenerated by introducing the fluorine source for reuse in further fluorination reactions.

The compounds of Formula I may be used to fluorinate organic compounds, for example nucleosides, nucleoside bases and steroids, or cationic organometallic compounds for example cyclopentadienides. They are especially useful in fluorinating carbanionic and/or aromatic substrates and in particular aromatic substrates having electron-withdrawing substituents, for example halo or nitro substituents.

In a preferred embodiment of the fluorination aspect invention, a fluorinated steroid is prepared by contacting a steroid or a suitable derivative such as a steroidal enol acetate or silyl enol ether with a fluorinating agent of Formula I optionally in the presence of a solvent and optionally at elevated temperature. Preferably, the steroid is fluorinated at the 6 and/or 16 position.

Compounds of Formula I may be isolated or used without separation from the reaction mixture. If desired, the reaction mixture may be fed to a separate fluorination reactor or the compound of Formula I may be purified or otherwise treated prior to use.

Accordingly, the invention also provides a method of producing a fluorinated substrate which comprises contacting, preferably under acidic conditions, a triazine compound with a fluorine source in a solvent, which is inert under the process conditions, such that at least one of the nitrogen atoms in the triazine compound is fluorinated to produce a compound of Formula I and contacting, in situ or subsequently, the compound with a substrate to be fluorinated.

The invention is illustrated by the following non-limiting Examples.

EXAMPLE 1

Preparation of 1-fluoro-2,4,6-trichloro-1,3,5-triazinium triflate

Cyanuric chloride (0.1 g, 0.54 mmol), triflic acid (0.08 g, 0.53 mmol) and acetonitrile (80 cm$^3$) were placed in the flow fluorination reactor, cooled to −35° C., stirred vigorously and treated with a 1:9 (v/v) fluorine-nitrogen blend (flow rate of 130 cm$^3$ per minute) until the exit gas gave a strong positive test (Kl) for fluorine. A small sample (20 cm$^3$) of the resulting colorless reaction solution was tested for oxidation properties with aqueous Kl and gave a strong positive result. A sample (20 cm$^3$) of the cold (−35° C.) reaction solution was treated with dry benzene (2.0 cm$^3$) and the homogeneous mixture left to warm to room temperature before being analyzed by $^{19}$F NMR, using D$_2$O as an external lock. The spectrum showed the characteristic absorption for fluorobenzene at δ$_f$−36.2 (m) ppm (TFA (trifluoroacetic acid) ref.). The remaining reaction solution was evaporated under reduced pressure, yielding a white solid which fumed in air. The $^{19}$F NMR spectrum of this fuming solid (dissolved in CD$_3$CN) was found to contain the expected OTf$^-$ absorption at 5.4(s) ppm (TFA ref.), as well as an absorption at 39.3 (br. s) ppm assignable to the $^+$NF function of 1-fluoro-2,4,6-trichloro-1,3,5-triazinium triflate. Owing to the highly hygroscopic nature of this white solid, a satisfactory elemental analysis was impossible to obtain; iodometric titration of a sample of this product revealed that the F$^+$content was 62% (i.e. the percentage of oxidizing F$^+$ present per mole of the reagent). The reaction was repeated using hexafluoroisopropanol as the fluorination solvent, but the material obtained was only 86% pure (estimated by $^{19}$F NMR).

EXAMPLE 2

Fluorinations using 1-fluoro-2,4,6-trichloro-1,3,5-triazinium tetrafluoroborate in $CD_3CN$ The required amount of 1-fluoro-2,4,6-trichloro-1,3,5-triazinium tetrafluoroborate was weighed into a glass vial in an efficient dry box (argon atmosphere) before it was added to a cold solution (0° C.) of the substrate in $CD_3CN$. The reaction mixture was allowed to warm to room temperature, transferred to a standard NMR tube and its spectrum measured.

1) Reaction with methoxybenzene

The reaction was carried out on both a 1:1 and 2:1 molar ratio basis (methoxybenzene: $^+$NF). In both experiments the reaction was immediate and exothermic, and the solution's changed color from yellow (at 0° C.) to dark violet at room temperature). After 8 hours, the $^{19}$F NMR spectra (188.8 MHz; 27° C.; $CFCl_3$) of the reaction solutions showed absorptions at $\delta_F$ (1:1 reaction)–126.6 (m, 4-F) and –137.8 (m, 2-F) and (1:2 reaction) –126.6 (m, 4-F) and –137.9 (m, 2-F) ppm (product ratio: 4-F:2-F, 2:1); other (unidentified) absorptions were observed at $\delta_F$–123.2, –123.3, –132.0, and –132.9 ppm.

2) Reaction with benzene

The reaction was carried out using a 1:1 molar ratio of reactants. A progressive color change of the reaction solution was observed [colorless (0° C. to room temperature, 1.0 hour), pale yellow (room temperature, 2.0 to 4.0 hours), yellow to pale brown (room temperature, 4.0 to 8.0 hrs)], and after 8.0 hours the $^{19}$F NMR ($CFCl_3$) spectrum was measured and found to contain only the characteristic absorption for fluorobenzene at $\delta_F$–115.2 (m) ppm and a $BF_4^-$ peak.

3) Reaction with chlorobenzene

The reaction was carried out on a 1:1 molar ratio basis. After 8.0 hours (room temperature; change from colorless to pale brown solution) the $^{19}$F NMR ($CFCl_3$) spectrum was measured and showed an absorption at $\delta_F$–116.0 (m, 4-F) ppm assignable to 4-chlorofluorobenzene.

4) Reaction with nitrobenzene

The reaction was carried out on a 1:1 molar ratio basis. After 8.0 hours (room temperature; colorless solution changed to pale brown), the $^{19}$F NMR ($CFCl_3$) spectrum of the product was measured and showed an absorption at $\delta_F$–109.4 (m, 3-F) which was more intense than an absorption associated with decomposition of 1-fluoro-2,4,6-trichloro-1,3,5-triazinium tetrafluoroborate (see below) and hence indicated that 3-fluoronitrobenzene had been formed.

5) $^{19}$F NMR examination of 1-fluoro-2,4,6-trichloro-1,3,5-triazinium tetrafluoroborate in $CD_3CN$ A solution of 1-fluoro-2,4,6-trichloro-1,3,5-triazinium tetrafluoroborate in $CD_3CN$ was made at room temperature (colorless) and its $^{19}$F NMR (ref. $CFCl_3$) spectrum was measured immediately; this showed absorptions at +15.3 (br.s., $^+$NF) ppm and –146.7 (br.s., $BF_4^-$) ppm. A number of minor peaks were observed in the region between $\delta_F$–1.0 and –110 ppm, suggesting that a decomposition of the $^+$NF salt was taking place. The sample was left standing for 2.0 hours (the solution's color changed to pale yellow) before the spectrum was measured again; this revealed that the intensity of $^+$NF absorption at $\delta_F$+15.3 had markedly decreased, while the intensities of the absorption peaks associated with decomposition of the salt ($\delta_F$–1.0 to –110 ppm) had noticeably increased. These minor absorptions were present in the spectra of all of the products from the above reactions.

EXAMPLE 3

Fluorinations using 1-fluoro-2,4,6-trichloro-1,3,5-triazinium tetrafluoroborate without solvent A suspension of 1-fluoro-2,4,6-trichloro-1,3,5-triazinium tetrafluoroborate (0.1 g, 3.4 mmol) and an excess of the substrate was prepared in a sealed tube at room temperature (using an argon-filled dry box). The mixture was heated to about 60° C. for a few minutes, then cooled to room temperature, before a small sample was syringed out and filtered to remove any insoluble materials (i.e. 1-fluoro-2,4,6-trichloro-1,3,5-triazinium tetrafluoroborate) before its $^{19}$F NMR ($CFCl_3$) spectrum was measured using $D_2O$ as an external lock.

1) Reaction with benzene

The $^{19}$F NMR spectrum of the product was measured immediately and showed the characteristic absorptions for monofluorobenzene at $\delta_F$–113.3(m) ppm and 1,4-difluorobenzene at $\delta_F$–119.9 ppm, with a ratio of approximately 2:1. A Kl test of the reaction mixture gave a strong positive result, indicating that the reaction had not gone to completion at this stage, and the reaction mixture was left standing at room temperature for 14 days (an excessive period, negative Kl test at this stage). The $^{19}$F NMR spectrum of the sample was then measured again and revealed the presence of another difluoro-isomer, namely 1,2-difluorobenzene [$\delta_F$–138.7 (m) ppm; the ratio of 1,4- to 1,2-$C_6H_4F_2$ was about 2:1].

2) Reaction with chlorobenzene

The 19F NMR spectrum of the product was measured shortly after the reaction had been carried out and found to contain absorptions at $\delta_F$–111.0 (m, 3-F); –115.7 (m, 2-F) and –116.1 (m, 4-F) (the ratio of 2-:3-:4-isomers was about 1:0.3:2). After 14 days (negative Kl test), the $^9$F NMR spectrum showed no evidence for the presence of any other products.

3) Reaction with nitrobenzene

The $^{19}$F NMR spectrum of the reaction solution contained one weak absorption assignable to 3-fluoronitrobenzene at $\delta_F$–110.27 (m) after about 25 minutes. After 14 days (positive Kl test still) however, the $^9$F NMR spectrum showed absorptions corresponding to 3-fluoronitrobenzene at $\delta_F$–110.3 (m) and 2-fluoronitrobenzene at $\delta_F$–119.1 (m) (ratio about 2:1); also, in keeping with the result of the Kl test, the $^+$NF absorption of the reagent was still present.

A homogeneous reaction mixture was obtained in this experiment, whereas in the aforementioned fluorinations of benzene and chlorobenzene, the reaction mixtures contained suspended [$(ClCN)_3F$]$^+BF_4^-$. In order to drive the fluorination of nitrobenzene to completion, the reaction mixture was heated at 90° C. for 2 hours before it was tested with Kl solution and gave a negative result. G. C. analysis revealed the presence of only 3-fluoronitrobenzene and 2-fluoronitrobenzene with no marked change in ratio (about 2:1 ratio). Despite the presence of the 2-fluoro derivative, no evidence was obtained for the presence of 4-fluoronitrobenzene. The absence of 4-fluoronitrobenzene may have resulted from loss of this isomer during the reaction or subsequent handling operations via nucleophilic displacement of the highly mobile fluorine. In this connection, the reaction vessel became etched during the reaction.

EXAMPLE 4

(i) Preparation of 1-fluoro-2,4,6-tris (trifluoromethyl)-1,3,5-triazinium triflate 2,4,6-Tris(trifluoromethyl)-1,3,5-triazine (0.2 g, 0.7 mmol), triflic acid (0.11 g, 0.73 mmol) and hexafluoroisopropanol (80 cm$^3$) were placed in a flow fluorination reactor, cooled (−5° C.), stirred vigorously and treated with a 1:9 (vol./vol.) fluorine-nitrogen blend (flow rate of 130 cm$^3$ per minute) until the exit gas gave a strong positive test (Kl) for fluorine. A small sample (10 cm$^3$) of the resultant colorless reaction solution was tested for oxidation properties with aqueous Kl and gave a strong positive test. The remaining reaction solution was evaporated under reduced pressure, yielding a colorless oily material, which fumed when exposed to air. The $^{19}$F NMR spectrum of this material (in CD$_3$CN) contained the expected OTf$^-$ and CF$_3$ at $\delta_F$+0.5–6.0 (s; TFA ref.) ppm as well as a weak absorption at +28.3 (br. s) assignable to the $^+$NF function of 1-fluoro-2,4,6-tris (trifluoromethyl)-1,3,5-triazinium triflate. The reaction was repeated a number of times, but no pure $^+$NF salt was isolated, believed to be due to the hygroscopic nature of $^+$NF salt and its reactivity towards water.

(ii) Fluorination of benzene with 1-fluoro-2,4,6-tris (trifluoromethyl)-1,3,5-triazinium triflate A sample (30 cm$^3$) of the cold (−5° C.) reaction solution from (i) above was treated with dry benzene (2.0 cm$^3$) and the homogeneous mixture left to warm to room temperature overnight before being analyzed by $^{19}$F NMR, using D$_2$O as an external lock. The spectrum showed the characteristic absorption for fluorobenzene at $\delta_F$−36.4 (m; TFA ref.) ppm.

EXAMPLE 5

(i) Preparation of 2,4,6-trimethoxy-1,3,5-triazine

Cyanuric chloride (5.0 g, 27 mmol) was added dropwise to a cold (−5° C.) stirred solution of sodium methoxide (5.0 g, 93 mmol) in dry methanol (50 cm$^3$); the mixture was then allowed to warm to room temperature and then refluxed for 3.0 hours. The reaction mixture was filtered to isolate inorganic salts and the filtrate freed from solvent (Rotavapor™) yielding an off-white solid which was dissolved in diethyl ether (50 cm$^3$). The ethereal solution was washed with water (3×30 cm$^3$), charcoaled, dried over MgSO$_4$ and finally evaporated (Rotavapor™) to give pure 2,4,6-trimethoxy-1,3,5-triazine (4.3 g, 25 mmol, 93%) as a crystalline white solid.

Product Analysis (2,4,6-trimethoxy-1,3,5-triazine):

M. P. 136° C. Found: C, 42.2; H, 5.1; N, 24.4%. Calculated for C$_6$H$_9$N$_3$O$_3$: C, 42.1; H, 5.3; N, 24.6%], $\delta^1$H (CDCl$_3$) 4.1 (s, 3×OCH$_3$) ppm, $\delta^{13}$C (CDCl$_3$) 175.5 (C=N), 58.4 (s, 3×OCH$_3$) ppm.

(ii) Production of 1-fluoro-2,4,6-trimethoxy-1,3,5-triazinium triflate

A homogeneous mixture of 2,4,6-trimethoxy-1,3,5-triazine (0.1 g; 0.585 mmol), triflic acid (0.1 g; 0.66 mmol) and acetonitrile (80 cm$^3$) was placed in a flow fluorination reactor, cooled to −35° C., stirred vigorously and treated with a 1:9 (volume/volume) blend of fluorine and nitrogen gas at a flow-rate of 130 cm$^3$/minute until the exit gas gave a strong positive test for fluorine (using potassium iodide).

The solution was concentrated under reduced pressure to 10 cm$^3$ and dry dichloromethane (30 cm$^3$) was added. A white solid material was obtained by suction filtration, and was washed with dry diethyl ether (30 cm$^3$) and dried in vacuo and characterized by elemental analysis and NMR spectroscopy as 1-fluoro-2,4,6-trimethoxy-1,3,5-triazinium triflate. The product (1-fluoro-2,4,6-trimethoxy-1,3,5-triazinium triflate) was obtained in a yield (0.18 g; 0.53 mmol) of 91% based on the triazine starting material.

Product Analysis (1-fluoro-2,4,6-trimethoxy-1,3,5-triazinium triflate):

M. P. 186° C.; Found: C, 23.4; H, 2.5; N, 11.8%. Calculated for C$_7$H$_9$F$_4$N$_3$O$_6$S. H$_2$O; C, 23.5; H, 3.1; N, 11.8%; $\delta_H$ H (CD$_3$CN, TMS (trimethylsilane)) 4.59 (s, 2×OCH$_3$), 4.42 (s, OCH$_3$) ppm.; $\delta_C$ (CD$_3$CN) 167.6 (s, C=N), 156.1 (q, CF$_3$SO$_3$$^-$, J$_{CF}$276 Hz), 61.2 (s, 2×OCH$_3$), 59.6 (s, OCH$_3$) ppm; $\delta_F$ (CD$_3$CN, TFA) 18.65 (br s, N$^+$F), 1.72 (s, CF$_3$SO$_3$$^-$) ppm.

EXAMPLE 6

Production of 1-fluoro-2,4,6-trimethoxy-1,3,5-triazinium triflate

The procedure of Example 5 was repeated except that hexafluoro-isopropanol was used as the solvent and the reaction was carried out at −5° C. The product (1-fluoro-2,4,6-trimethoxy-1,3,5-triazinium triflate) was characterized using elemental analysis and NMR spectroscopy and obtained in a yield of 98%.

EXAMPLE 7

Production of 1-fluoro-2,4,6-trimethoxy-1,3,5-triazinium hexafluoroantimonate The procedure of Example 6 was repeated except that the reactants employed were 2,4,6-trimethoxy-1,3,5-triazine (0.5 g; 2.92 mmol) and hexafluoroantimonic acid (0.69 g; 2.92 mmol) and diethyl ether (50 cm$^3$) instead of dichloromethane was used in the "work-up". The product (1-fluoro-2,4,6-trimethoxy-1,3,5-triazinium hexafluoroantimonate) was characterized by NMR spectroscopy and elemental analysis and obtained in a yield (1.22 g; 2.86 mmol) of 98%.

Product Analysis (1-fluoro-2,4,6-trimethoxy-1,3,5-triazinium hexafluoroantimonate):

M. P. 211° C. (dec). Found: C, 17.1; H, 1.9; N, 9.5; Sb, 28.9%. Calculated for C$_6$H$_9$F$_7$N$_3$O$_3$Sb: C, 17.0; H, 2.1: N, 9.9; Sb, 28.6%; $\delta_H$ (CD$_3$CH, TMS) 4.59 (s, 2×OCH$_3$), 4.44 (s, OCH$_3$) ppm; $\delta_C$CN)1.67 (s, C=N), 61.1 (s, 2×OCH$_3$), 59.4 (s, OCH$_3$) ppm; $\delta_F$ (CD$_3$CN, TFA) 18.88 (br s, N$^+$F), −20.75 to −79.96 (complex, SbF$_6$$^-$) ppm. The structure was confirmed by single crystal X-ray analysis (bond length: F—N, 1.354 Å).

EXAMPLE 8

(i) Preparation of 2,4,6-trimethyl-1,3,5-triazine

A stainless steel pressure vessel (100 cm$^3$) was charged with dry acetonitrile (10.0 g, 244 mmol) and yttrium triflate (1.07 g, 2 mmol). The vessel was cooled (−196° C.), evacuated and charged with anhydrous ammonia (4.2 cm$^3$, 247 mmol), sealed and then heated for 24 hours at 200° C. The autoclave was cooled to room temperature before the volatile material (unchanged ammonia) was allowed to bleed off. Diethyl ether (300 cm$^3$) was added to the reaction mixture and the insoluble material removed by filtration, dissolved in ethyl acetate (30 cm$^3$), washed with water (3×20 cm$^3$), dried with MgSO$_4$ then evaporated (Rotavapor™) to give 4-amino-2,6-dimethylpyrimidine (22.0 g, 179 mmol, 73%) as a crystalline white solid.

Product Analysis (4-amino-2,6-dimethylpyrimidine):

M. P. 184° C. Found: C, 58.2; H, 7.5; N, 34.3%. Calculated for C$_6$H$_9$N$_3$:C, 58.5; H, 7.4; N, 34.2%; δ$_H$ (CD$_3$CH, TMS) 6.0 (s, HC=C), 5.2 (br.s, NH$_2$), 2.2 (s, CH$_3$) and 2.1 (br.s, CH$_3$) ppm.

Rotary evaporation of the ethereal solution provided 5.0 g (41 mmol, 17%) of an off-white solid; this was purified by vacuum sublimation to give pure 2,4,6-trimethyl-1,3,5-triazine as a crystalline white solid.

Product Analysis (2,4,6-trimethyl-1,3,5-triazine):

M. P. 56° C. Found: C, 58.3; H, 7.6; N, 33.8%. Calculated for C$_6$H$_9$N$_3$: C, 58.5; H, 7.3; N, 34.2%; δ$_H$ (CD$_3$CN$_3$, TMS) 2.52 (s, 3×CH$_3$) ppm; δ$_C$ (CDCl$_3$) 176.3 (s, C=N), 25.8 (s, CH$_3$) ppm.

(ii) Production of 1-fluoro-2,4,6-trimethyl-1,3,5-triazinium triflate

The procedure of Example 5 was repeated except that that the reactants employed were 2,4,6-trimethyl-1,3,5-triazine (0.1 g) and triflic acid (0.12 g). The product (1-fluoro-2,4,6-trimethyl-1,3,5-triazinium triflate) was characterized using elemental analysis and NMR spectroscopy as hexahydrated 1-fluoro-2,4,6-trimethyl-1,3,5-triazinium triflate and obtained in a yield of 68%.

Product Analysis (1-fluoro-2,4,6-trimethyl-1,3,5-triazinium triflate):

M. P. 205° C. (dec); Found: C, 21.8; H, 3.0; N, 9.7%. Calculated for C$_7$H$_9$F$_4$N$_3$O$_3$S. 6H$_2$O: C, 21.1; H, 5.3; N, 10.5%; δ$_H$ (CD$_3$CN, TMS) 2.4 (d., 2×CH$_3$), 2.1 (s, CH$_3$) ppm.; δ$_C$ (CD$_3$CN) 178.4 (s, C=N), 168.6 (q, CF$_3$ J$_{CF}$287.3 Hz), 26.6 (s, 2×CH$_3$), 23.5 (s, CH$_3$) ppm; δ$_F$ $_{(CD3}$CN$_3$, TFA) 1.43 (s, CF$_3$) 19.2 (br s, N$^+$F) ppm.

EXAMPLES 9 to 18

Production of a variety of 1-fluoro-2,4,6-trimethoxy-1,3,5-triazinium salts

A variety of salts were produced using different acids and with different ratios of acid to substrate as set out in Table 1. The procedure of Example 5 was followed in producing these salts.

TABLE 1

| Example | Acid | Acid:substrate (moles) | $^+$N—F % yield |
|---|---|---|---|
| 9 | Triflic | 1.1:1 | 89[b] |
| 10 | Triflic | 1.5:1 | 76[b] |
| 11 | Triflic | 2:1 | 5 |
| 12 | Sulfuric (98%) | 1.2:1 | 91[b] |
| 13 | Sulfuric (98%) | 2:1 | 82[b] |
| 14 | Tetrafluoroboric (48%) | 1.1:1 | 77[a] |
| 15 | Tetrafluoroboric (48%) | 2:1 | 23[a] |
| 16 | Trifluoroacetic | 1.8:1 | 92[a] |
| 17 | Acetic | 2.1:1 | 85[a] |
| 18 | Anhydrous hydrogen fluoride | 1:1 | 94[a] |

[a]Determined by $^1$H and $^{19}$F NMR.
[b]Isolated material.

As shown by Table 1, the yield of 1-fluoro-2,4,6-trimethoxy-1,3,5-triazinium salts was sensitive to the amount of Brønsted acid used in the synthesis. When a 1.5 or less molar equivalent of triflic acid was used, the simple triflate salt of the triazine was obtained in high yields. However, the use of more than 1.5 molar equivalents of triflic acid caused the yield of the $^+$N—F salt to depreciate greatly and mainly the $^+$N—H salt was produced. Similar results were obtained with other acids.

EXAMPLE 19

Fluorination of phenyl lithium using 1-fluoro-2,4,6-trimethoxy-1,3,5-triazinium triflate 1 Mole of phenyl-lithium (in dry diethyl ether) was added dropwise to a stirred suspension of 1 mole of 1-fluoro-2,4,6-trimethoxy-1,3,5-triazinium triflate in dry diethyl ether at a temperature of about −70° C. The mixture was stirred for 2 hours and then allowed to warm slowly to room temperature overnight with continuous stirring. The reaction mixture was filtered and distilled. The residue was analyzed by 19F NMR spectroscopy (in CDCl$_3$; TFA ref.) and showed the characteristic absorption for fluorobenzene at δ$_F$−36.2 ppm.

Attempts to fluorinate benzene or methoxybenzene using 1-fluoro-2,4,6-trimethoxy-1,3,5-triazinium triflate or 1-fluoro-2,4,6-trimethyl-1,3,5-triazinium triflate under similar conditions to those successfully used in Example 19 to fluorinate phenyl lithium were unsuccessful indicating that 1-fluoro-2,4,6-trichloro-1,3,5-triazinium triflate is a significantly stronger fluorinating agent than either 1-fluoro-2,4,6-trimethoxy-1,3,5-triazinium triflate or 1-fluoro-2,4,6-trimethyl-1,3,5-triazinium triflate.

EXAMPLE 20

Fluorinations using 1-fluoro-2,4,6-trichloro-1.3,5-triazinium tetrafluoroborate in nitromethane A solution of 1-fluoro-2,4,6-trichloro-1,3,5-triazinium tetrafluoroborate (0.1 g, 3.4 mmol) and the substrate in equimolar proportion was prepared in nitromethane (20 cm$^3$) in a sealed tube at room temperature (except for the reaction involving methoxybenzene), using an argon-filled dry box. Reaction progress was determined by removing small samples via a syringe and subjecting them to $^9$F NMR analysis (CFCl$_3$ ref.; D$_2$O ext. lock).

1) Reaction with methoxybenzene

The reaction was carried out on both a 1:1 and 2:1 molar ratio basis (methoxybenzene:$^+$NF). In both experiments the reaction was immediate and exothermic, and the solutions changed color from colorless (at about −20° C.) to dark violet (at room temperature). After 2.0 hours (-ve Kl test), the $^{19}$F NMR spectra (188.8 MHz; 27° C., CFCl$_3$) of the reaction solutions showed absorptions at δ$_F$ (1:1 reaction) −126.6 (m, 4-F) and −137.8 (m, 2-F), and (1:2 reaction) −126.6 (m, 4-F) and −137.9 (m, 2-F) ppm (product ratio: 4-F:2-F=2:1).

2) Reaction with benzene

The $^{19}$F NMR spectrum of the product was measured immediately and showed the characteristic absorptions for monofluorobenzene at δ$_F$−113.3 (m) ppm and 1,4-difluorobenzene at δ$_F$−119.9 ppm, with a ratio of approximately 2:1. A Kl test on the reaction mixture gave a strong positive result, indicating that the reaction had not gone to completion at this stage, hence, the reaction mixture was heated to 70° C. and its $^{19}$F NMR spectrum measured at intervals to determine the progress of reaction. After 2.0 hours, the spectrum showed only absorptions for fluorobenzene and 1,4-difluorobenzene and the reaction mixture still gave a positive Kl test. However, after 6.0 hours a negative Kl test was obtained, indicating that consumption of the NF reagent was complete, and $^{19}$F NMR analysis revealed the presence of another difluorinated isomer, namely 1,2-difluorobenzene [$\delta_F$–138.7 (m) ppm; the ratio of 1,4- to 1,2-$C_6H_4F_2$ was about 2:1].

3) Reaction with chlorobenzene

The $^{19}$F NMR spectrum of the reaction solution was measured shortly after it had been prepared and found to contain absorptions at $\delta_F$–111.0 (m, 3-F); –115.7 (m, 2-F) and –116.1 (m, 4-F) (the ratio of 2-: 3-: 4-isomers was about 1:0.3:2). After heating the solution at 70° C. for 6.0 hours (negative Kl test), its $^{19}$F NMR spectrum showed no evidence for the presence of any other products.

4) Reaction with nitrobenzene

The $^{19}$F NMR spectrum of the reaction solution contained one weak absorption assignable to 3-fluoronitrobenzene at $\delta_F$–110.27 (m) after about 25 minutes. After 6.0 hours of heating at 70° C. (positive Kl test still) however, the $^{19}$F NMR spectrum showed absorptions corresponding to 3-fluoronitrobenzene at $\delta_F$–110.3 (m) and 2-fluoronitrobenzene at $\delta_F$–119.1 (m) (ratio about 2:1); also, in keeping with the result of a Kl test (weakly positive), the $^+$NF absorption of the reagent was still present.

EXAMPLE 21

Preparation of 1-fluoro-2,4,6-trichloro-1,3,5-triazinium triflate in nitromethane Cyanuric chloride (0.1 g, 0.54 mmol), triflic acid (0.08 g, 0.53 mmol) and nitromethane (80 cm$^3$) were placed in a flow fluorination reactor, cooled (about –30° C.), stirred vigorously and treated with a 1:9 (v/v) fluorine-nitrogen blend (flow-rate 130 cm$^3$ per minute) until the exit gas gave a strong positive test (Kl) for fluorine. A small sample (20 cm$^3$) of the resulting colorless reaction solution was tested for oxidation properties with aqueous Kl and gave a strong positive result. A sample (20 cm$^3$) of the cold (about –30° C.) reaction solution was treated with dry benzene (2.0 cm$^3$) and the homogeneous mixture left to warm to room temperature before being analyzed by $^{19}$F NMR, using $D_2O$ as an external lock. The spectrum showed the characteristic absorption for fluorobenzene at $\delta_F$–36.2 (m) ppm (TFA ref.). The remaining reaction solution was allowed to warm to room temperature (it remained clear and colorless) then evaporated under reduced pressure, yielding an off-white solid which fumed profusely in air. The $^{19}$F NMR spectrum of this fuming solid (dissolved in $CH_3NO_2$ and using $D_2O$ as an external lock) was found to contain the expected OTf$^-$ absorption at 5.4 (s) ppm (TFA ref.), as well as an absorption at 39.3 (br. s) ppm assignable to the $^+$NF function of 1-fluoro-2,4,6-trichloro-1,3,5-triazinium triflate. Owing to the highly hygroscopic nature of this white solid, no further analysis was obtained.

The above reaction was repeated using $CH_3NO_2$ diluted with $CHCl_3$ (mixtures containing 10%, 50% and 80% of $CH_3NO_2$ were studied) as a solvent. Fluorination proceeded more cleanly as the proportion of nitromethane increased; thus, while use of neat $CH_3NO_2$ or 80% $CH_3NO_2$ produced clean, colorless reaction solutions at room temperature, use of the lower concentrations of $CH_3NO_2$ gave colored solutions (dark brown at 10% concentration; pale yellow at 50%), again after the reaction solutions had warmed to ambient temperature.

It will be appreciated that the invention is not restricted to the details described above with reference to the preferred embodiments but that numerous modifications and variations can be made without departing from the scope or spirit of the invention.

We claim:

1. A method of electrophilic fluorination which comprises contacting an organic substrate with a N-fluorotriazinium salt electrophilic fluorinating agent, wherein said electrophilic fluorination comprises introducing a carbon-flourine bond into the substrate.

2. The method according to claim 1, wherein the N-fluorotriazinium salt electrophilic fluorinating agent has the following Formula I:

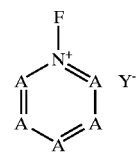

(I)

wherein:

three A moieties are independently CR, where each R is independently selected from the group consisting of hydrogen, halogen, hydroxyl, (primary, secondary or tertiary) amino, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

two A moieties are independently Z, where each Z is independently nitrogen or a quaternary nitrogen atom; and Y$^-$ is a counterion or group of counterions which are inert to chemical attack by fluorine, or is an oligomer or polymer thereof in which adjacent triazinium moieties are linked by a common R substituent.

3. The method according to claim 2, wherein the N-fluorotriazinium salt is a N-fluoro-1,2,4-triazinium compound of the following Formula IA:

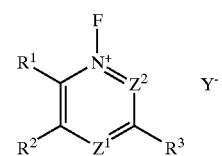

(IA)

wherein:

R$^1$, R$^2$ and R$^3$ are, independently, selected from the group consisting of hydrogen, halogen, hydroxyl, (primary, secondary or tertiary) amino, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

Z$^1$ and Z$^2$ are independently nitrogen or a quaternary nitrogen atom and Y$^-$ is a counterion or group of counterions which are inert to chemical attack by fluorine, or is an oligomer or polymer thereof in which adjacent triazinium moieties are linked by a common R substituent.

4. The method according to claim 2, wherein the N-fluorotriazinium salt is a N-fluoro-1,3,5-triazinium compound of the following Formula IB:

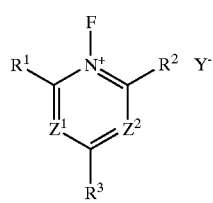

(IB)

wherein:

$R^1$, $R^2$ and $R^3$ are, independently, selected from the group consisting of hydrogen, halogen, (primary, secondary or tertiary) amino, hydroxyl, cyano, perfluorothio, hydroxysulfonyl, halosulfonyl, hydrocarbyloxysulfonyl, or a carbon-containing substituent selected from the group consisting of optionally substituted hydrocarbyl, hydrocarbyloxy, hydrocarbyloxycarbonyl, and hydrocarbylthio groups;

$Z^1$ and $Z^2$ are independently nitrogen or a quaternary nitrogen atom and $Y^-$ is a counterion or group of counterions which are inert to chemical attack by fluorine, or is an oligomer or polymer thereof in which adjacent triazinium moieties are linked by a common R substituent.

5. The method according to claim 2, wherein the R substituents, or $R^1$, $R^2$ and $R^3$, are selected from the group consisting of halogen and trifluoromethyl.

6. The method according to claim 5, wherein the R substituents, or $R^1$, $R^2$ and $R^3$, are selected from the group consisting of chlorine, fluorine and trifluoromethyl.

7. The method according to claim 5, wherein an unsubstituted aromatic substrate or an aromatic substrate having one or more electron-withdrawing substituents is contacted with a N-fluoro-trihalotriazinium salt.

8. The method according to claim 7, wherein the aromatic substrate is selected from the group consisting of chlorobenzene and nitrobenzene.

9. The method according to claim 2, wherein the substrate is an electron-rich species.

10. The method according to claim 9, wherein the electron-rich species is a carbanionic substrate.

11. The method according to claim 9, wherein the electron-rich species is an activated aromatic substrate.

12. The method according to claim 9, wherein the electron-rich species is steroid or derivative thereof.

13. The method according to claim 2, wherein the R substituents, or $R^1$, $R^2$ and $R^3$, are identical.

14. The method according to claim 13, wherein each R, or each of $R^1$, $R^2$ and $R^3$ chlorine.

15. The method according to claim 2, wherein both Z, or both of $Z^1$ and $Z^2$, is nitrogen or a fluorinated quaternary nitrogen.

16. The method according to claim 15, wherein both Z, or both of $Z^1$ and $Z^2$, is nitrogen.

17. The method according to claim 16, wherein the N-fluorotriazinium salt is a N-fluoro-1,3,5-triazinium compound of the following Formula II:

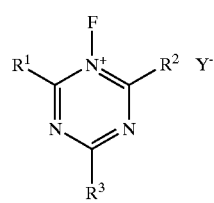

(II)

wherein $R^1$, $R^2$, $R^3$ and $Y^-$ are as defined in claim 1.

18. The method according to claim 16, wherein the N-fluorotriazinium salt is a N-fluoro-2,4,6-trichloro-1,3,5-triazinium compound of the following Formula IIA:

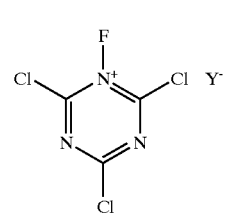

(IIA)

wherein $Y^-$ is a counterion or group of counterions which are inert to chemical attack by fluorine.

19. The method according to claim 2, wherein $Y^-$ is selected from the group consisting of fluoride, fluorosulfate, alkanesulfonate, alkyl sulfate, perfluoroalkanesulfonate, arenesulfonate, alkanecarboxylate; perfluoroalkanecarboxylate, tetrafluoroborate, tetraphenylborate, hexafluorophosphate; hexafluoroantimonate; hexafluoroarsenate; chlorate; sulfate (=2$Y^-$), hydrogen sulfate and $F(HF)_x^-$ where x is at least 1.

20. The method according to claim 19, wherein $Y^-$ is selected from the group consisting of fluoride, tetrafluoroborate, triflate, tosylate, hexafluoroarsenate and hexafluorophosphate.

21. The method according to claim 14, wherein $Y^-$ is triflate.

22. A method of electrophilic fluorination which comprises contacting an organic substrate with a N-fluoro-1,3,5-triazinium compound of the following Formula II, wherein said electrophilic fluorination comprises introducing a carbon-fluorine bond into the substrate;

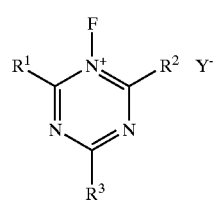

(II)

wherein;

$R^1$, $R^2$, and $R^3$ are selected from the group consisting of halogen and trifluoromethyl and $Y^-$ is selected from the group consisting of fluoride, fluorosulfate, alkanesulfonate, alkyl sulfate, perfluoroalkanesulfonate, arenesulfonate, alkanecarboxylate; perfluoroalkanecarboxylate, tetrafluoroborate, tetraphenylborate, hexafluorophosphate; hexafluoroantimonate; hexafluoroarsenate; chlorate; sulfate (=2$Y^-$), hydrogen sulfate and $F(HF)_x^-$ where x is at least 1.

23. The method according to claim 22, wherein $R^1$, $R^2$ and $R^3$ are selected from the group consisting of chlorine, fluorine and trifluoromethyl and $Y^-$ is selected from the group consisting of fluoride, tetrafluoroborate, triflate, tosylate, hexafluoroarsenate and hexafluorophosphate.

24. The method according to claim 23, wherein $R^1$, $R^2$ and $R^3$ are all chlorine.

* * * * *